United States Patent [19]

Poshkus

[11] Patent Number: 4,528,386

[45] Date of Patent: Jul. 9, 1985

[54] SYNTHESIS OF 2,4,8,10-TETROXASPIRO[5.5]UNDECANE

[75] Inventor: Algirdas C. Poshkus, Lancaster, Pa.

[73] Assignee: The United States of America as represented by the Administrator of the National Aeronautics and Space Administration, Washington, D.C.

[21] Appl. No.: 183,707

[22] Filed: Sep. 3, 1980

Related U.S. Application Data

[63] Continuation of Ser. No. 54,502, Jul. 3, 1979, abandoned.

[51] Int. Cl.$^3$ ............................................. C07D 319/00
[52] U.S. Cl. ................................................... 549/335
[58] Field of Search ...................... 260/340.7; 549/335

[56] References Cited

U.S. PATENT DOCUMENTS

| | | | |
|---|---|---|---|
| 1,934,309 | 11/1933 | Hoover | 260/340.7 |
| 2,775,622 | 12/1956 | Snow | 260/340.7 |
| 2,915,530 | 12/1959 | Kray et al. | 260/340.7 |
| 2,945,008 | 7/1960 | Caldwell et al. | 260/340.7 |
| 3,092,640 | 6/1963 | Mantell et al. | 260/340.7 |
| 4,076,727 | 2/1978 | Rey et al. | 260/340.9 R |

*Primary Examiner*—Ethel G. Love
*Attorney, Agent, or Firm*—Darrell G. Brekke; John R. Manning; Robert D. Marchant

[57] ABSTRACT

Pentaerythritol can be converted to its diformal, 2,4,8,10-tetroxaspiro[5.5]undecane, by heating it to a temperature within the range of about 110° to 150° C. for a period of up to 10 minutes, in the presence of a slight excess of paraformaldehyde and of a catalytic quantity of an acid catalyst such as sulfuric acid. The reaction may be carried out in two steps, by forming first the monoformal, then the diformal. In any case, total reaction time is about 10 minutes and yield of diformal are greater than 90%.

Previous processes require hours or days, and often, tedious operating procedures.

6 Claims, No Drawings

SYNTHESIS OF 2,4,8,10-TETROXASPIRO[5.5]UNDECANE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

This is a continuatioin of application Ser. No. 054,502, filed July 3, 1979, now abandoned.

BACKGROUND OF THE INVENTION

1. Field of the Invention

The present invention relates to 2,4,8,10-tetroxaspiro[5.5]-undecane(pentaerythritol diformal) and more particularly to an improved method for its preparation.

2. Description of the Prior Art

Pentaerythritol diformal is readily prepared, often in good yield, under acidic conditions from pentaerythritol and aqueous formaldehyde, trioxane, or paraformaldehyde. Reaction times, however, are in the order of several hours or days, and operations for its isolation can be time-consuming. These conventional processes may be illustrated by that of A. Skrabal et al [Z. Physik. Chem., 119, 305 (1926)] which consists in heating pentaerythritol in trioxane, on a waterbath, for 4 hours in order to obtain a 75% yield of the spirocyclic formal. Formation of the diformal from chloromethyl ethers of pentaerythritol and of 5,5-bis(hydroxymethyl)-1,3-dioxane has no practical synthetic value [J. Lichtenberger et al, Bull. Soc. Chim. France, 468 (1947)]. As to the reaction of paraformaldehyde with paraldehyde to obtain the diformal, it requires at least 30 hours for a 15% yield by tedious operations [H. J. Prins, Rec. Trav. Chim. 71, 1131 (1952)].

The more recent efforts in the preparation of various acetals of pentaerythritol still offer no clues on the possible improvement of the conventional preparations of pentaerythritol diformal. Renner et al (U.S. Pat. No. 3,978,088), for instance, prepare diacetals with dimeric $\beta$-OH-pivaldehyde in hydrochloric acid by a 24 hour reaction. Fruhstorfer et al (U.S. Pat. No. 3,621,034), on the other hand, boil pentaerythritol with dodecylthiopropanol for 3½ hours, while Kray et al (U.S. Pat. No. 2,915,530) obtain their diacetals with e.g. acrolein after a 4 hour reflux period in the presence of 0.1% phosphoric acid.

Finally, Zey et al (U.S. Pat. No. 4,076,727) most recently disclosed the preparation of cyclic acetal from polyols, e.g. trimethylolpropane and an aldehyde such as formaldehyde and butyraldehyde, by refluxing such compounds in, e.g. benzene for a period of at least 4 hours. The possibility of higher temperatures, i.e., up to 150° C., is mentioned, solvent permitting it is assumed. In any event, Zey et al appear to be committed to a conventional process to obtain the acetals that they need for the synthesis of acrylic esters.

In summary, the processes that have just been reviewed, as well as several other existing approaches, variously suffer from one or more of the following shortcomings, namely: long reaction times—hours or days; inferior yield of product; time-consuming procedures for isolation; use of solvents; high expenditure of energy; and inadaptability to continuous production.

In view of this situation, it is the principal object of this invention to provide a process which will be free of any and all of the art limitations just enumerated.

SUMMARY OF THE INVENTION

It has now been discovered that pentaerythritol diformal can be prepared conveniently in high yield in less than 10 minutes, simply by heating a stirred mixture of pentaerythritol with paraformaldehyde in slight excess, at a temperature of up to about 120° C. in the presence of a catalytic quantity of acid, in the absence of any solvent except for a small quantity of water.

DETAILED DESCRIPTION OF THE INVENTION

To obtain the desired cyclic diformal of pentaerythritol, a powdered mixture of the tetrahydroxy compound and a slight excess of paraformaldehyde is heated rapidly while stirring to a temperature above 100° C. and as high as 150° C., but preferably within the range of 110°-130° C. Total heating time lasts from about 5 to 10 minutes. During this heating, the mixture turns into a paste, progressively becoming more fluid as the temperature rises, and finally turning into a clear liquid at about 110° C. Between about 105° and 115° C., the liquid boils as the water of reaction escapes, then it soon becomes quiescent. The clear odorless liquid crystallizes into a solid mass of crystals on cooling. The product supercools rapidly, evolving an appreciable quantity of heat during solidification. It also melts within the range of 35° to 48° C.—in the lower end of the range if some monoformal is present, and in the upper range, if the reaction has been properly carried out to minimize formation of the monoformal. Recrystallization from petroleum ether or distillation will yield the pure compound melting at 50° C.

The reaction is advantageously carried out in two steps. First, the reagents are heated to a maximum temperature of about 120° for about 5 minutes to give the monoformal. After cooling to about 70° and adding the second molar equivalent of paraformaldehyde, with about 1% excess, the mixture is heated again to about 120° for about 5 minutes to convert the monoformal to the diformal. In this manner, the total heating time is still about 10 minutes, but formaldehyde losses are minimized and conversion is improved, although yields are in excess of 90° in either case.

Catalytic quantities of acid, i.e. about 0.1 to 1.0 mole %, must be present. Examples of usable acids include hydrochloric, sulfuric, toluenesulfonic, and methanesulfonic acids, as well as boron trifluoride etherate and aluminum chloride. Hydrochloric acid is used advantageously with zinc chloride, but this acid may be objectionable because of possible formation of the carcinogenic bis(chloromethyl)ether. Cadmium chloride, zinc chloride, or phosphoric acid in low concentrations are ineffective; only resinous products or rubbery gels are formed from which no diformal can be isolated. However, when a small quantity of water is used with zinc chloride, moderate yields of the diformal are produced. Although only clear resins or tough rubbery gels are produced with small concentrations of phosphoric acid (<10 mole %, based on pentaerythritol), with larger concentrations of the acid, the diformal is obtained in increasingly better yields, e.g. 80% when an equimolar quantity of acid is present.

If anhydrous acids are used, a small quantity of water, about 1% of the total weight of the reactants, is beneficial in that the reagents convert into an easily stirrable fluid much faster. Heat transfer is thus greatly improved. Aside from this convenience, water is not essential for good yield of product.

Instead of paraformaldehyde, trioxane is considerably more expensive and, when the reaction is incomplete, difficult to separate from the diformal. Formalin, i.e. 40% aqueous formaldehyde, gives the diformal as the art shows, but the reaction takes longer due to longer boiling to remove water and some diformal is lost in the water vapor.

The following examples will now illustrate the practice of the invention in operational detail. In all the preparations described, the reagents are of commercial quality and are employed as received, except for occasional powdering of solids, as necessary.

EXAMPLE 1

A mixture of pentaerythritol, 40.8 g, paraformaldehyde, 20 g, and sulfuric acid, 5 drops, was heated to 145° C. in about 10 minutes and maintained at this temperature until ebullition ceased, about 5 minutes. On cooling to room temperature, the clear liquid obtained solidified exothermally into a crystalline mass weighing 48.6 g. Extraction with boiling petroleum ether and distillation of the extracts left the diformal as white needles, 33.5 g, mp 49°-50°. The immiscible oil remaining was mixed with paraformaldehyde, 1.5 g, and heated rapidly to 150° C. for a total of 10 minutes. Work-up as before gave a second crop of diformal, 11.2 g, mp 49°-50° C., for a total yield of 92% based on the pentaerythritol.

EXAMPLE 2

A mixture of pentaerythritol, 13.0 g, paraformaldehyde, 3.1 g, and 25% sulfuric acid, 2.0 g, was heated in 1 minute to 105° C. The paste, initially formed at 65° C., became a thin slurry at 70° C. and a clear liquid at 105° C. After 2 minutes at 105°-110° C. and another 2 minutes at 115°-120° C., the liquid was cooled to 80° C. and additional paraformaldehyde, 3.1 g, was added. Heating was continued as before, and the reaction mixture then cooled to get a crystalline white solid, 15.8 g, mp 45°-48° C., which after extraction with petroleum ether gave 14.5 g of the diformal.

EXAMPLE 3

A mixture of paraformaldehyde, 7.0 g, pentaerythritol, 13.6 g, zinc chloride, 0.6 g, and concentrated hydrochloric acid, 1.0 ml, was heated in 4 minutes to 100° C. to give a clear liquid which boiled at 114° C. for 2 minutes and was quiescent at 120° C. for 2 minutes. On cooling, it solidified to a solid cake, 16.8 g, mp 42°-48° C. A solution of the product was treated with charcoal and sodium carbonate and filtered to remove the zinc chloride. Distillation of the solvent left the diformal, 15.7 g, mp 46°-48° C.

EXAMPLE 4

A mixture of pentaerythritol, 27.2 g, paraformaldehyde, 13.6 g, methanesulfonic acid, 5 drops, was heated to 150°-160° C. in 15 minutes and maintained at this temperature for a total heating time of 30 minutes. The liquid solidified to a white waxy solid, 28.0 g. Extraction with petroleum ether and distillation of the extracts left the diformal, 22.9 g, mp 49°-50° C. The oily residue, immiscible in petroleum ether, was combined with the similar oil from an earlier run, 2.0 g, and heated with paraformaldehyde, 2.0 g, for 15 minutes to get another crop of diformal, 6.5 g, mp 48°-50° C.

EXAMPLE 5 p-Toluenesulfonic acid, 0.2 g, was mixed with powdered pentaerythritol, 13.6 g, and paraformaldehyde, 6.2 g, and heated to 150° C. for a total time of 15 minutes to get the crude diformal, 15.5 g, mp 37°-42° C.

EXAMPLE 6

Zinc chloride, 0.3 g, and water, 4 drops, were mixed with pentaerythritol, 13.6 g, and paraformaldehyde, 6.8 g. This reaction mixture was heated in 3 minutes to 90° C., when it became a putty-like mass, and then a paste at 100° C. At 120°-125° C., the viscous bubbling paste turned into a clear liquid after 10 minutes. The temperature was raised to 145° C. for 3 minutes, and the pale brown liquid cooled to a waxy solid, 14.8 g, mp 38°-43° C. The diformal, 10.4 g, mp 49°-50° C., was extracted from this wax with petroleum ether. When water was excluded from this reaction mixture, only 0.8 g of the diformal could be extracted from the viscous reaction product.

EXAMPLE 7

Pentaerythritol, 13.6 g, paraformaldehyde, 6.9 g, and 85% phosphoric acid, 11.0 g, were heated up to 150° C. for a total time of 10 minutes. The diformal was extracted from the resultant ether miscible viscous oil with methylene chloride for a yield of 12.5 g, mp 46°-48° C.

EXAMPLE 8

Repeating the procedure of Example 7 with only 0.3 g of the phosphoric acid and heating for a total time of 12 minutes yielded a very viscous oil which on cooling became a tacky cololess resin, 15.6 g, insoluble in either methylene chloride or ether. No diformal was found.

EXAMPLE 9

A mixture of pentaerythritol, 13.6 g, paraformaldehyde, 6.2 g, and boron trifluoride etherate, 4 drops, was heated in 4 minutes to 105° C. to give a clear liquid. At 120° C., boiling occurred, which ceased in about 5 minutes, after which the temperature was held at 130° C. for 3 minutes. When the liquid cooled, the oily crystalline product was extracted with petroleum ether to yield the diformal, 9.1 g, mp 48°-49° C.

EXAMPLE 10

Pentaerythritol, 13.6 g, paraformaldehyde, 3.1 g, sulfuric acid, 0.5 g, and water, 1.5 g, were heated together to form a paste in 0.5 minute at 65° C. and a thin slurry at 90° C. in 1 minute. At 100°-110° C., the slurry was converted into a clear liquid in 0.5 minute. Heating at 100°-110° C. was continued for 2 minutes and finally at 115°-120° C. for another 2 minutes. The liquid, 16.1 g, was cooled to about 60° C. and paraformaldehyde, 3.1 g, added. The slurry was heated at 110° C. to obtain a clear liquid and then for about 2 minutes at 115°-125° C., for a total heating time of 5 minutes. The liquid solidified to a white crystalline mass, 15.8 g, mp 45°-48° C.

EXAMPLE 11

A mixture of trioxane, 6.3 g, pentaerythritol, 13.6 g, and sulfuric acid, 4 drops, was heated rapidly to a thin slurry at 100° C. that clarified within 5 minutes at 110°

C. The temperature was raised to 150° C., during which time much boiling occurred but soon subsided, heating was continued for 5 minutes. The total heating time was 20 minutes. The diformal, 5.7 g, mp 48°–50° C., was extracted with petroleum ether. The oil immiscible with petroleum ether, 8.6 g, was heated rapidly to 155° C. with paraformaldehyde, 1.5 g, for a total heating time of 10 minutes to get a second crop of the diformal, 6.7 g, mp 48°–50° C.

The improved process of the invention has several advantages over the processes of the art in terms of shortened reaction times in the order of 3 to 20 minutes, yields greater than 90%, elimination of solvents, decrease in labor and energy requirements, adaptability to continuous operations, and overall simplicity and convenience. The product, of course, can be used for its conventional purposes which, inter alia, include conversion into ethylenically unsaturated monomers, into aphrogenic and pyrostatic phosphorylated derivatives, and the like. It is further contemplated that many variations can be carried out by the man skilled in the art without departing from the limits of the present invention as claimed.

What is claimed is:

1. A process for the preparation of the cyclic diformal of pentaerythritol, which comprises providing a mixture of pentaerythritol and paraformaldehyde in approximately stoichiometric proportions, such mixture being substantially anhydrous and solvent-free, and heating such mixture in the presence of an acid catalyst to a temperature between about 105° and 150° C. thereby causing the mixture to liquify and continuing such heating for a total period of about 3 to 20 minutes to cause and complete the reaction of pentaerythritol with paraformaldehyde to produce the diformal of pentaerythritol, and during such heating allowing the water resulting from the reaction to evaporate.

2. The process of claim 1 wherein up to about 1% by weight of water is present in the reaction mixture.

3. The process of claim 1 wherein about 0.1 to 1.0 mole %, based on the pentaerythritol of an acid catalyst is used, said acid catalyst being selected from the group consisting of sulfuric acid, hydrochloric acid, methanesulfonic acid, p-toluenesulfonic acid, boron trifluoride etherate, zinc chloride, aluminum chloride, and mixtures thereof.

4. The process of claim 1 wherein the acid catalyst is concentrated aqueous phosphoric acid present in a concentration greater than 10 mole %, based on the pentaerythritol.

5. The process of claim 1 wherein the reaction is carried out in two stages, with about one-half of the paraformaldehyde being added at each stage and heated with the other components for a period about half as long as the total heating time.

6. The process of claim 1 wherein the reaction is carried at a temperature within the range of about 110° to 130° C. for a period of up to 10 minutes.

* * * * *